US012595358B2

(12) United States Patent
Mott et al.

(10) Patent No.: US 12,595,358 B2
(45) Date of Patent: Apr. 7, 2026

(54) ENHANCEMENT OF RUBBER BY HEAT-ASSISTED MIGRATION FROM ANCILLARY RUBBER

(71) Applicant: The Government of the United States of America, as represented by the Secretary of the Navy, Arlington, VA (US)

(72) Inventors: Peter H. Mott, Washington, DC (US); Howard L. Schrader, White Plains, MD (US); Nickolaus K. Weise, Alexandria, VA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 455 days.

(21) Appl. No.: 18/329,516

(22) Filed: Jun. 5, 2023

(65) Prior Publication Data

US 2023/0391992 A1     Dec. 7, 2023

Related U.S. Application Data

(60) Provisional application No. 63/348,503, filed on Jun. 3, 2022.

(51) Int. Cl.
| | |
|---|---|
| *C08L 11/00* | (2006.01) |
| *A61J 3/00* | (2006.01) |
| *A61K 9/70* | (2006.01) |
| *C08K 5/00* | (2006.01) |
| *C08K 5/18* | (2006.01) |
| *C08K 5/57* | (2006.01) |

(52) U.S. Cl.
CPC ................ *C08L 11/00* (2013.01); *A61J 3/00* (2013.01); *A61K 9/7023* (2013.01); *C08K 5/005* (2013.01); *C08K 5/0058* (2013.01); *C08K 5/18* (2013.01); *C08K 5/57* (2013.01); *A61J 2200/42* (2013.01)

(58) Field of Classification Search
None
See application file for complete search history.

(56) References Cited

U.S. PATENT DOCUMENTS

| | | | | |
|---|---|---|---|---|
| 3,426,473 | A | * | 2/1969 | Cardarelli ............... B32B 27/00 |
| | | | | 428/905 |
| 4,913,976 | A | * | 4/1990 | Brooks .................... B60J 10/79 |
| | | | | 428/494 |
| 5,123,985 | A | * | 6/1992 | Evans ...................... B29D 7/01 |
| | | | | 425/389 |
| 5,227,157 | A | * | 7/1993 | McGinity .............. A61K 31/44 |
| | | | | 424/78.02 |
| 7,413,694 | B2 | * | 8/2008 | Waldrop, III ......... B29C 70/544 |
| | | | | 264/102 |
| 2004/0099603 | A1 | | 5/2004 | Livingston |
| 2006/0182976 | A1 | * | 8/2006 | Yamakawa ............. B32B 25/02 |
| | | | | 428/521 |

FOREIGN PATENT DOCUMENTS

| | | | |
|---|---|---|---|
| CN | 1767944 | A | 5/2006 |
| CN | 201756239 | U | 3/2011 |
| CN | 107033421 | A | 8/2017 |
| CN | 107488270 | A | 12/2017 |

OTHER PUBLICATIONS

Search Report and Written Opinion in PCT/US2023/067946.

* cited by examiner

*Primary Examiner* — Christopher M Rodd
(74) *Attorney, Agent, or Firm* — US Naval Research Laboratory; Joseph T. Grunkemeyer

(57) ABSTRACT

A method of restoring an elastomer by providing an article containing a first elastomer and having a surface, contacting the surface with a layer conformal to the surface, and applying heat and pressure to the layer. The layer contains a second elastomer and a solute. The heat and pressure induce a transfer of the solute from the layer to the article.

14 Claims, 3 Drawing Sheets

ENHANCEMENT OF RUBBER BY HEAT-ASSISTED MIGRATION FROM ANCILLARY RUBBER

This application claims the benefit of U.S. Provisional Application No. 63/348,503, filed on Jun. 3, 2022. The provisional application and all other publications and patent documents referred to throughout this nonprovisional application are incorporated herein by reference.

TECHNICAL FIELD

The present disclosure is generally related to restoration of elastomer and rubber materials.

DESCRIPTION OF RELATED ART

Common rubbers or elastomers are susceptible to degradation by oxygen and ozone; this causes the stiffness to change (either increase or decrease), a loss of elongation, and cracking, and many other problems. To prevent this, rubber compounds in nearly all commercial products contain a small percentage of antioxidants and antiozonants, to preserve the properties of the rubber. They quench the free radicals that form when the respective oxygen and ozone species react with the double bond within the backbone of the rubber macromolecule. They generally have a small molecular weight (ca. 250 Daltons) and their concentration are a few percent (ca. 2-5 weight %).

One such antioxidant, n-phenyl-β-naphthylamine, functions by providing hydrogen from its amine group to the free radicals formed during oxidation, to become a radical itself. This radical is stabilized by the resonance delocalization of the electrons within the aromatic rings. In the process, the antioxidant is consumed, and after some period, the rubber gradually becomes susceptible to oxidation as the antioxidant is depleted. At this stage, the mechanical degradation of the rubber will accelerate, and it will soon fail. Thus, depletion of the antioxidant determines service life.

In addition, rubber is sometimes employed to provide a desired chemical agent (such as a therapeutic compound, odorant, or biocide) at a controlled rate to an external environment, application, or process. The agent is normally incorporated during the initial mixing of the elastomer, which is then crosslinked using heat and pressure. In such cases, the chemical agent may be dissolved into the rubber compound, which becomes depleted as the agent is released. It is also possible that the desired chemical agent was not included in the original elastomer mixing, possibly due to its tendency to degrade, or otherwise interfere with vulcanization.

BRIEF SUMMARY

Disclosed herein is a method comprising: providing an article comprising a first elastomer and a surface; contacting the surface with a layer conformal to the surface; wherein the layer comprises a second elastomer and a solute; and applying heat and pressure to the layer to induce a transfer of a portion of the solute from the layer to the article.

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein is a process to add desired chemical agent(s) to a rubber, after the rubber has been cured. The implementation described herein uses diffusion accelerated by heat, from a single-use rubber sheet that contains a higher concentration of the desired agent, to a rubber article that is to be enhanced, restored, or rejuvenated.

Figure 1:
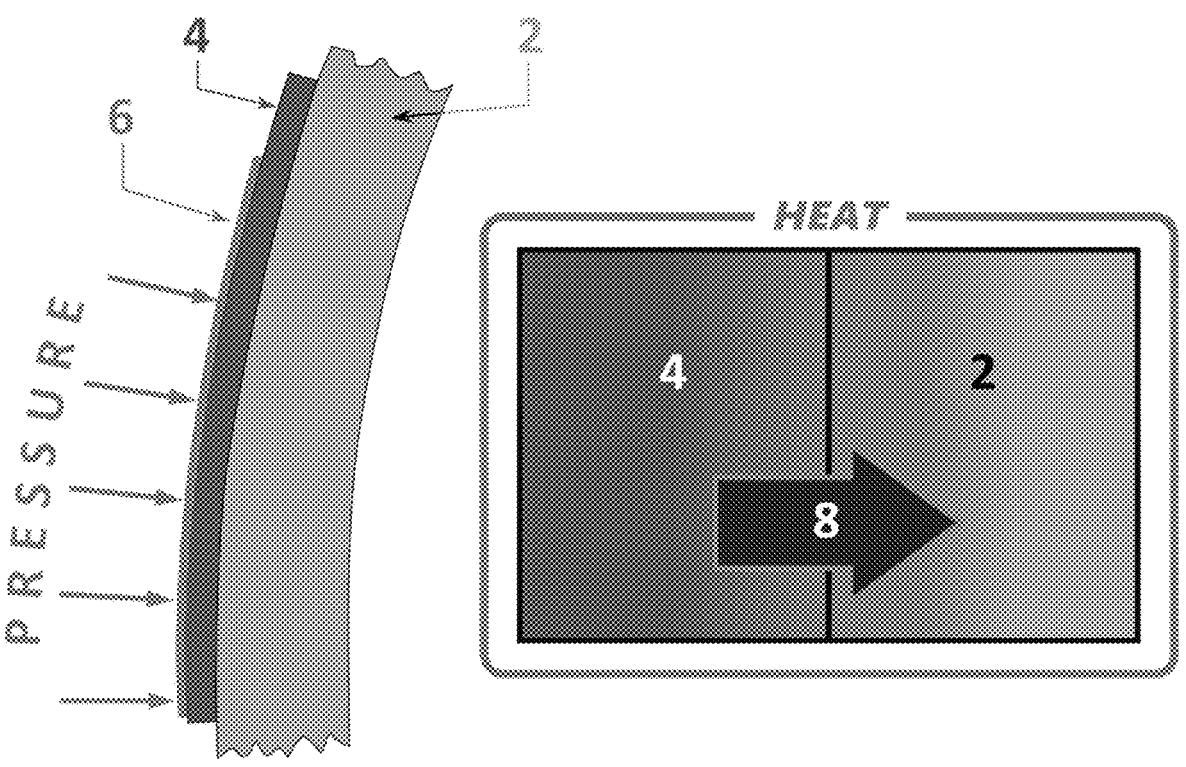
FIG. 1 schematically illustrates the present method. Left: Heater 6, source rubber 4, and target rubber 2. Pressure is applied to ensure the source rubber is in full contact with the target rubber. Right: Migration of the desired chemical agent 8, from the source rubber 4 to the target rubber 2. Migration is accelerated by increasing the temperature.

The concentration of the desired chemical agent 8 is increased in the target rubber 2, by placing a source rubber sheet 4, which has a high concentration of the desired chemical agent, in contact with the target rubber. When the system is heated, the desired chemical agent migrates from the source rubber to the target rubber (FIG. 1). The process of the migration is simple diffusion of the dissolved desired chemical agent in the rubber, from high to low concentration.

The process variables include the composition of the source rubber, its concentration of the desired chemical, and the heating time and temperature. The structure of the backbone molecule, additives, crosslink chemistry, etc., in the source rubber, may be quite different from the target rubber. The higher the temperature and the longer the heating time, the greater amount of the desired chemical agent that is transferred into the target. However, this must be balanced with rubber degradation, or other losses, of the desired chemical. Higher concentration of the desired chemical in the source rubber also provides more transfer, but this must be balanced with inferior mechanical and chemical properties of the source rubber. To provide a greater transfer, the process can be carried out more than once, using a new source rubber for each heating cycle.

In a first step, a rubber article is provided. The article comprises a first elastomer and a surface. The first elastomer may be, for example, polychloroprene rubber. The article may also comprise a less-than-desired amount of a solute, such as a biocide, an anti-ozonant, an anti-oxidant, or a therapeutic agent.

Next, the surface is contacted with a layer of material or a blanket that conforms to the surface. The entire surface or a portion of the surface may be in such contact. The layer comprises a second elastomer and the solute. The second elastomer may be the same as or different from the first elastomer and may be, for example polychloroprene rubber. The solute may be, for example, bis(tri-n-butyltin)oxide or n-phenyl-β-naphthylamine.

Next, heat and pressure are applied to the layer to induce a transfer of a portion of the solute from the layer to the article. At least some or up to an equilibrium amount of the solute is transferred. The transfer may be verified by known analytical techniques. After the transfer, the process may be repeated with additional blankets to further increase the concentration of the solute in the article.

Figure 2:
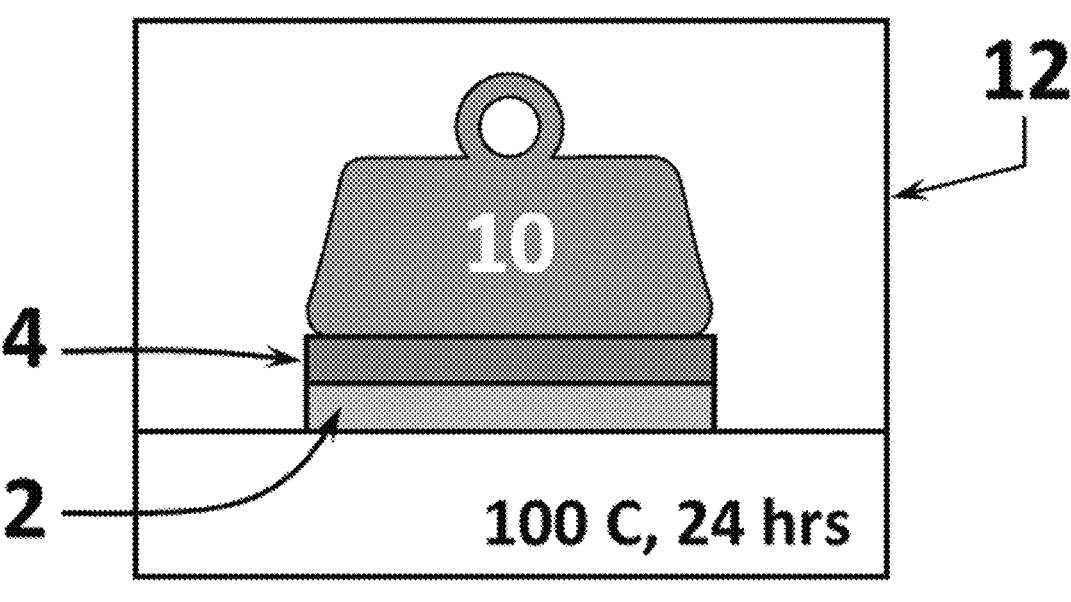
FIG. 2 schematically illustrates a laboratory test demonstration. A thin sheet of the source rubber 4 is placed on top of the target rubber 2, and placed beneath a 6 kg weight 10. The rubber sheets were put in an oven 12, with the temperature is maintained at 100° C. for 24 hours.

The principles behind the method were tested in laboratory experiments shown schematically in FIG. 2. For this test, two small thin rubber samples (dimensions 50 mm×50 mm×3 mm) were cut, from (1) a polychloroprene rubber sheet that contained 8.7 weight % hexabutyldistannoxane (also known as bis(tri-n-butyltin)oxide, or simply TBTO), a small molecule that is used an anti-fouling biocide, and (2) from a polychloroprene rubber sheet with zero TBTO. The samples were stacked beneath a 6 kg weight, with the TBTO-rich rubber on top, within a laboratory oven with ambient atmosphere, maintained at 100 C. After 24 h the samples were removed and the tin concentration was measured.

The composition of the rubbers in this test matched the proprietary composition of so-called NOFOUL® rubber, a trademark of Goodrich Inc, used to control fouling on US Navy ships. During shipboard service, fouling is prevented by leaching of TBTO from the rubber. As the TBTO is expended, NOFOUL® rubber becomes less effective. For the laboratory test herein, the target rubber had zero TBTO concentration, but all other components were the same as NOFOUIL®, thus mimicking TBTO depletion from NOFOUL® rubber that occurs during service.

The tin concentration was determined by x-ray fluorescence spectroscopy. The method uses the intensity of the tin $K_\alpha$ x-ray fluorescence peak (25.27 keV), calibrated with rubber samples of known TBTO concentrations. In this measurement, both the TBTO and the rubber it is dissolved in, absorb the x-rays, which limits the depth at which the tin concentration can be detected. The characteristic penetration depth of the $K_\alpha$ peak is about 1.5 mm. Consequently, the tin concentration is an average, weighted by distance from the surface, over this characteristic depth. As the method only detects tin, the results are provided as weight % tin. A new sheet of NOFOUL® rubber contains 5.78 weight % TBTO, which corresponds to 2.30 weight % tin.

The results of the laboratory experiment are shown in Table 1. It demonstrates that tin was transferred from the source rubber into the target rubber, the latter of which initially had zero tin. There was no other source of tin in the rubber compound.

TABLE 1

Figure 3:
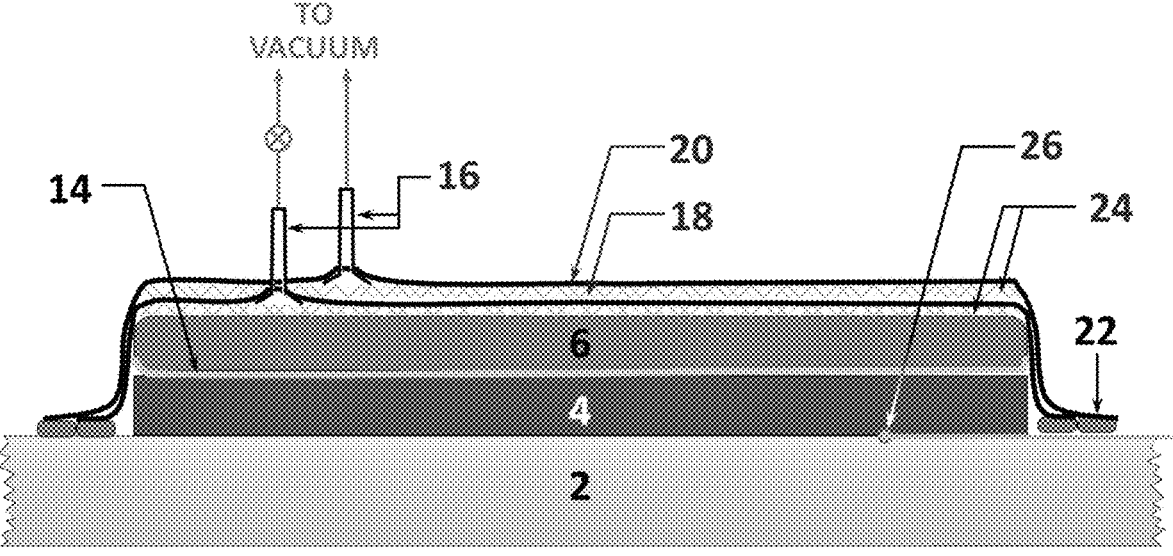
FIG. 3 schematically illustrates a larger scale test. The target rubber 2 was a large rubber part that was depleted of TBTO, that had been stored outside for 30 years. The source rubber 4, aluminum foil barrier 14, heater 6, were held against the part by applying a vacuum, to two encapsulating bags using through-bag fittings 16. The inner encapsulating bag 18 prevented loss of TBTO; it was initially evacuated, but then the valve to the vacuum pump was shut, to prevent TBTO loss while the system is heated. The outer bag 20 had vacuum applied throughout the process, to provide contact pressure between the source and the target rubber. The bags were sealed using tacky tape 22, and air passage within them was provided by breather blanket 24. The heat and vacuum were maintained for 24 h, at 90, 100, and 110° C., controlled using a thermocouple 26, placed between the source and the target rubber, to measure the temperature.

TBTO concentrations of rubber sheets shown in FIG. 3, before and after soaking in oven for 24 h at 100° C., in air. The tin concentration measurements were determined from the $K_\alpha$ peak. The tin concentration of 3.453 wt % corresponds to a TBTO concentration of 8.7 wt %.

| Sample | Surface | Tin Concentration (wt %) | |
| | | Before | After |
| --- | --- | --- | --- |
| TBTO- | Top | 3.453 ± 0.020 | 3.200 ± 0.020 |
| rich rubber | Contact | 3.425 ± 0.020 | 2.710 ± 0.020 |
| TBTO- | Contact | 0 | 0.741 ± 0.024 |
| free rubber | Bottom | 0 | 0.117 ± 0.024 |

Figure 4:
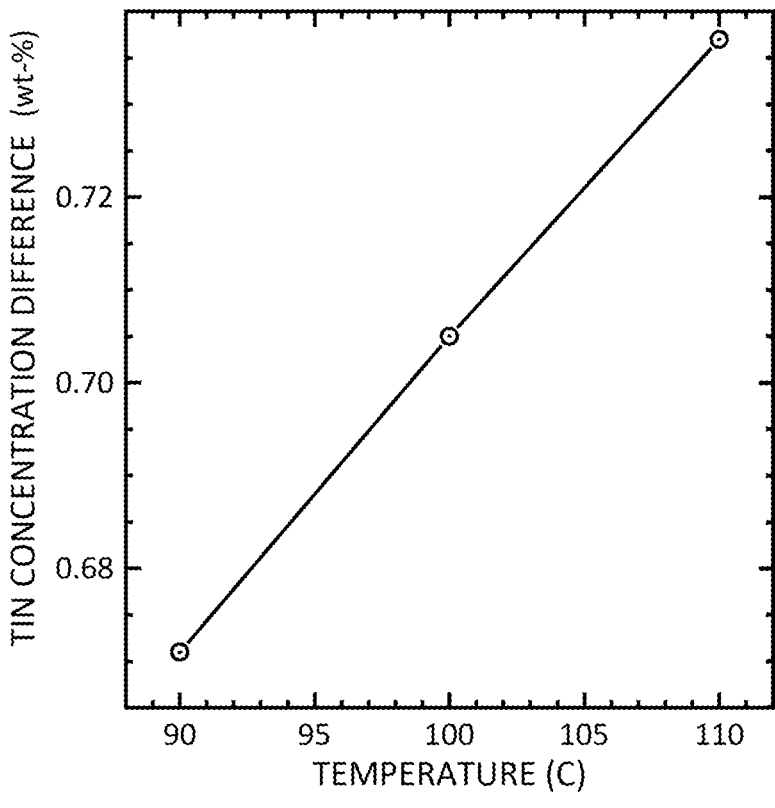
FIG. 4 shows a plot of the increase in tin concentration of the three patches from the larger scale test, as shown in Table 2. Heating time was 24 h.

A larger scale test was then carried out. The sample was a large rubber part that had been in ship service for eleven years and was mostly depleted of TBTO. The part was removed in 1991 and stored outside for 30 years. Immediately prior to the test, the rubber part was surveyed using x-ray fluorescence spectroscopy, and three representative areas that had nearly equal TBTO concentration were selected. Those areas were cleaned, and patches (150 mm×300 mm×3 mm) shown in FIG. 3 were installed. The vacuum was applied, and the patches were respectively heated to 90, 100, and 110° C. for 24 h, followed by tin concentration measurement. Table 2 lists these results, and FIG. 4 plots the concentration increase. Over this temperature range, it was observed that the increase was roughly linear with temperature.

TABLE 2

TBTO concentrations of rubber before and after soaking for 24 h under the patch shown in FIG. 4, at the indicated temperatures. The tin concentration measurements were determined by averaging eight x-ray fluorescence measurements; the variance is the standard deviation of the measurements.

| Temperature (° C.) | Tin Concentration (wt %) | | |
| | Before | After | Difference |
| --- | --- | --- | --- |
| 90 | 0.832 ± 0.023 | 1.503 ± 0.113 | 0.671 |
| 100 | 0.812 ± 0.049 | 1.517 ± 0.188 | 0.705 |
| 110 | 0.871 ± 0.011 | 1.606 ± 0.077 | 0.737 |

The method may be used to restore any chemical that has become depleted from a rubber part, such as antioxidants and antiozonants. It may also be used to add chemical agents to any rubber that is desirable to contain such agents, regardless of whether such agents originally within the rubber.

The use of a rubber source simplifies handling of what may be a dangerous, volatile, toxic, unpleasant, or otherwise difficult to manage chemical agent. The flexibility of the rubber allows it to be easily cut and fitted against any complex shape without gaps, ensuring that the desired agent is uniformly distributed into the target rubber. Any agent that was not transferred remains in the source rubber, which may be disposed without loss or spillage into the environment.

The time and temperature of the transfer process can be adjusted in many ways as familiar to the art, to provide exceptional accuracy of the amount of agent transferred.

The method makes it possible to extend the service life of large, expensive rubber parts, for far lower cost than that of replacing the part.

Many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:

1. A method comprising:

providing an article comprising a first elastomer and a surface;

contacting the surface with a layer conformal to the surface;

wherein the layer comprises a second elastomer and a solute;

applying heat and pressure to the layer to induce a transfer of a portion of the solute from the layer to the article; and separating the layer from the article.

2. The method of claim 1, wherein the first elastomer is polychloroprene rubber.

3. The method of claim 2, wherein the second elastomer is polychloroprene rubber.

4. The method of claim 1, wherein the solute is a biocide.

5. The method of claim 1, wherein the solute is bis(tri-n-butyltin)oxide.

6. The method of claim 1, wherein the solute is an anti-ozonant or anti-oxidant.

7. The method of claim 1, wherein the solute is n-phenyl-β-naphthylamine.

8. The method of claim 1, wherein the article is a medicinal patch.

9. The method of claim 8, wherein the solute is a therapeutic agent.

10. The method of claim 1, wherein applying heat is performed by placing the article and the layer in an oven.

11. The method of claim 1, wherein applying heat is performed by contacting the layer with a heater conformal to the layer.

12. The method of claim 1, wherein applying pressure is performed by placing a weight on the layer.

13. The method of claim 1, wherein applying pressure is performed by placing the layer and the article in an outer bag and drawing a vacuum on the outer bag.

14. The method of claim 13, wherein the layer and the article are encapsulated in an inner bag inside the outer bag.

* * * * *